United States Patent [19]

Thys-Jacobs

[11] Patent Number: 5,354,743
[45] Date of Patent: Oct. 11, 1994

[54] METHOD FOR THE TREATMENT OF PREMENSTRUAL SYNDROME WITH VITAMIN D

[76] Inventor: Susan Thys-Jacobs, 135 Hickory Grove Dr., New York, N.Y. 10538

[21] Appl. No.: 945,319

[22] Filed: Sep. 15, 1992

[51] Int. Cl.$^5$ .................... A61K 31/59; A61K 31/595
[52] U.S. Cl. .................... 514/167; 514/170; 514/171; 552/653
[58] Field of Search ............. 514/167, 171, 170; 552/653

[56] References Cited

U.S. PATENT DOCUMENTS

| | | | |
|---|---|---|---|
| 3,077,437 | 2/1953 | Heckel | 514/167 |
| 3,608,075 | 9/1971 | Glen et al. | 424/238 |
| 3,639,599 | 2/1972 | Mehrhof et al. | 424/239 |
| 4,035,504 | 7/1977 | Hidy et al. | 424/279 |
| 4,076,811 | 2/1978 | Lachnit-Fixson et al. | 424/239 |
| 4,145,416 | 3/1979 | Lachnit-Fixson et al. | 424/238 |
| 4,225,596 | 9/1980 | DeLuca | 514/167 |
| 4,241,087 | 12/1980 | Mir et al. | 424/324 |
| 4,252,797 | 2/1981 | Rosenthal | 424/201 |
| 4,291,028 | 9/1981 | Vorys | 424/201 |
| 4,315,033 | 2/1982 | Lawarson | 424/238 |
| 4,372,951 | 2/1983 | Vorys | 424/239 |
| 4,415,554 | 11/1983 | Horrobin | 424/145 |
| 4,439,432 | 3/1984 | Peat | 424/240 |
| 4,495,181 | 1/1985 | Norman et al. | 514/167 |
| 4,497,800 | 2/1985 | Larson et al. | 544/2 |
| 4,521,410 | 6/1985 | Holick et al. | 514/26 |
| 4,542,026 | 9/1985 | Rios | 514/345 |
| 4,588,716 | 5/1986 | DeLuca et al. | 514/168 |
| 4,590,184 | 5/1986 | Maeda et al. | 514/167 |
| 4,650,668 | 3/1987 | Barron et al. | 424/44 |
| 4,738,856 | 4/1988 | Clark | 426/74 |
| 4,946,679 | 8/1990 | Thys-Jacobs | 424/682 |
| 5,037,823 | 8/1991 | Jones et al. | 514/222.8 |
| 5,063,221 | 11/1991 | Nishii et al. | 514/167 |
| 5,075,499 | 12/1991 | Walsdorf et al. | 562/590 |
| 5,104,864 | 4/1992 | DeLuca et al. | 514/167 |

OTHER PUBLICATIONS

Cummings, S. and Ullman, D., "Menstrual Cramps and Premenstrual Syndrome (PMS)", Everybody's Guide to Homeopathic Medicines, 149–150 (1991).

Seikus, P., "Vitamin Therapy Studied As PMS Treatment", Better Nutrition 50(2) 14–15 (1988).

Kendall, K. et al., "The Effects of Vitamin B6 Supplementation on Premenstrual Symptoms", Obstet. and Gynecol. 70(2): 145–149 (1987).

Sheikh, M. S. et al., "Gastrointestinal Absorption of Calcium From Milk and Calcium Salts", N. Engl. J. Med. 317: 532–536 (1987).

Maddocks, S. et al., "A double-blind placebo-controlled trial of progresterone vaginal suppositories in the treatment of premenstrual syndrome", Am. J. Obstet. Gynecol, 154(3): 573–581 (1986).

Harrison, H., "Self-Help for Premenstrual Syndrome", Random House 1–5, 10–12, 25–28, 75–77, 104–106 (1985).

Price, W. A., et al., "Premenstrual Tension Syndrome", Resident and Staff Physician, 31(5):35 (1985).

Muse, K. N., et al., "The Premenstrual Syndrome", N. Engl. J. Med. 311: 1345–1349 (1984).

Abraham, G. E., "Nutritional Factors in the Etiology of the Premenstrual Tension Syndromes", J. Reproductive Med., 28(7): 446–464 (1983).

London, R. S., et al., "The Effect of α-Tocopherol on Premenstrual Symptomatology: A Double-Blind Study", J. An. Coll. Nutr., 2: 115–122 (1983).

(List continued on next page.)

Primary Examiner—Frederick Waddell
Assistant Examiner—T. S. Criares
Attorney, Agent, or Firm—Pennie & Edmonds

[57] ABSTRACT

A method for the treatment of premenstrual syndrome (PMS) by administering a therapeutically effective dose of vitamin D to an individual manifesting symptoms of PMS. In a case control study of 46 women (26 with PMS and 20 asymptomatic controls) women exhibiting PMS symptomatology had noticeably lower vitamin D levels than the women who were asymptomatic controls.

7 Claims, 2 Drawing Sheets

OTHER PUBLICATIONS

Abraham, G. E., "Magnesium deficiency in premenstrual tension", Magnesium Bull. 4: 68–72 (1982).

Reid, R. L., et al., "Premenstrual syndrome", Am. J. Obestet, Gynecol. 139(1): 86–97 (1981).

Handbook of Non-Prescription Drugs, 1979, 6th Edition, pp.239–245.

Haynes, R. C. and Murad, F., "Agents Affecting Calcification: Calcium, Parathyroid Hormone, Calcitonin, Vitamin D and Other Compounds", Goodman and Gillman's The Pharmological Basis of Therapeutics, 6th Ed., Chapter 65 pp. 1524–1529 (1980).

Argonz, J. and Abinzano, C., "Premenstrual Tension Treated With Vitamin A", J. Clin. Endocrinol. Metab. 10:1579 (1950).

Zondek, B. and Brzezinski, A., "Inactivation of Oestrogenic Hormone By Women with Vitamin B Deficiency", Br., J. Obstet, Gynicol. 55: 273 (1948).

Greenhill, J. P., and Freed S. C., "The Electrolyte Therapy of Premenstrual Distress", JAMA 117: 504 (1941).

Israel, S. L., "Premenstrual Tension", JAMA 110: 721 (1938).

Frank, R. T., "The Hormonal Causes of Premenstrual Tension", Arch, Neurol. Psychiatr. 26: 1053 (1931).

Price, W. A. and Giannini, A. J., "Premenstrual Tension Syndrome", Resident and Staff Physician, 31(5):34–38 (1985).

METHOD FOR THE TREATMENT OF PREMENSTRUAL SYNDROME WITH VITAMIN D

INTRODUCTION

The present invention is directed to a method for the treatment of premenstrual syndrome (PMS) with vitamin D. The method of the invention involves treating an individual who exhibits symptoms of PMS with a therapeutically effective dose of vitamin D.

The invention is illustrated by way of example, using a case control study which was conducted in 46 women (26 with PMS and 20 asymptomatic controls) to evaluate the chemical, hormonal and nutritional deficiencies manifest in women exhibiting PMS symptomatology. The medical, dietary and psychological histories of each woman were evaluated. Complete blood counts were taken, and chemistries were analyzed to determine albumin, alkaline phosphatase, magnesium, calcium, cholesterol levels. Additionally, calcium regulating hormones were measured, including intact parathyroid hormone, 25 hydroxyvitamin D, and 1,25 dihydroxyvitamin D. The dietary evaluation included measurement, over a 3 day period, of calories, protein, CHO, calcium, magnesium, cholesterol, sodium, and potassium. Dual photon absorptiometry was performed with respect to the lumbar spine and the proximal femur.

The results of this study demonstrated that some women manifesting PMS symptomatology exhibited lower 25 hydroxyvitamin D levels (FIG. 1) than their asymptomatic controls. The significant difference in vitamin D levels between women with PMS and asymptomatic controls shows that this vitamin has a role in both symptomatology and as a potential treatment for PMS in those women who demonstrate low vitamin D levels.

BACKGROUND OF THE INVENTION

Premenstrual Syndrome (PMS) is characterized by the cyclic recurrence of a variety of emotional and physical symptoms that occur before menses and subside with the onset of menstruation. The temporal occurrence of these symptoms during the luteal phase, rather than their nature, seems to define this phenomenon. The precise pathophysiology remains conjectural and obscure, although much has been written. Symptoms can range from mild to incapacitating. It has been estimated that as much as 90% of all premenopausal women have some degree of premenstrual symptoms and approximately 10 to 20% have severe and incapacitating symptoms. This latter population has been estimated to be about 7 million women.

Numerous hypotheses have been proposed to explain the underlying pathophysiology in PMS. These have included hormonal imbalances such as estrogen excess, progesterone deficiency, fluid retention, allergies, and alteration of endogenous opiates. Multiple therapeutic modalities have been prescribed without scientific foundation and without any significant clinical success.

Recently however, substantial success in this area has been achieved. For example, U.S. Pat. No. 4,946,679 to Thys-Jacobs teaches a method for the treatment of PMS by administering a therapeutically effective dose of calcium to an individual manifesting symptoms of PMS. Calcium plays a role in the release of neurotransmitters, endocrine and exocrine products, in the contraction of skeletal and smooth muscle, and metabolism. Menstruation is related to ovarian and pituitary secretory function. The '679 patent discloses that calcium, coupled with ovarian linked hormones, may modulate the intrinsic feedback mechanisms that translate physiologic neuroendocrine and hormonal messages into behavioral and somatic changes.

While calcium is very important in reducing the symptomalogy of PMS of most PMS sufferers, the clinical trial discussed herein reveals that vitamin D also has a role in the pathophysiology of PMS for those women who demonstrate low vitamin D levels.

SUMMARY OF THE INVENTION

Vitamin D, or 25 hydroxyvitamin, plays an important role in PMS symptomatology for certain women. A vitamin D deficiency or partial deficiency has an adverse effect on normal cellular physiology and function, resulting in the multitude of symptoms such as fatigue, lack of concentration, irritability, mood disturbances and breast fullness commonly seen in women suffering with PMS.

Vitamin D has multiple known functions. In the intestine, 1,25(OH)2 increases the absorption rate of calcium, phosphorus and magnesium throughout the small and large bowels. 1,25(OH)2D increases the transport of calcium from the extracellular to intracellular space, and it can mobilize intracellular calcium concentrations from intracellular calcium pools. Vitamin D induces the synthesis of proteins in the intestinal epithelial cell and affects the lipid composition of intestinal brush border epithelial cells. Receptors for 1,25(OH)2 are present in many organs and tissues. They have been found in the intestines, kidneys, bone, skin, breast, pituitary gland, parathyroid glands, beta cells of the pancreatic islets, gonads, brain, skeletal muscle, circulating monocytes and lymphocytes.

Vitamin D deficiency has also been shown to impair insulin secretion and glucose tolerance, and to impair normal cellular differentiation. Furthermore, vitamin D deficiency has been associated with chronic muscle weakness and myopathy. The precise physiologic role vitamin D has in all these tissues in unclear, and what the pathophysiological interaction is between vitamin D and PMS symptomatology remains to be determined. However, the significant difference in vitamin D levels between the women with PMS and asymptomatic controls proves that this vitamin has a role in PMS symptomatology.

Vitamin D may be commenced on the day of diagnosis, regardless of when the individual's menstrual period begins, and should continue long term. Treatment of PMS should include vitamin D supplements and may be administered in any appropriate form. In a preferred embodiment of the invention, the vitamin D is administered orally in the forms of vitamin D2 (ergocholecaliferol) or vitamin D3 (cholecalciferol), or calcifediol [25(OH)]. Vitamin D may be administered intramuscularly as well.

Depending upon the severity of symptoms and the degree of deficiency present, initial treatment with vitamin D2 or Vitamin D3 can range from 200 to 1,000 IU daily or, for individuals exhibiting a marked deficiency, 50,000 to 200,000 IU weekly for 2 to 3 months. Calcifediol or 25(OH)D3 can be used in dosages of 20 or 200 ug (800–80,000 IU) per day for 2–4 weeks. Far lower doses can then be used long term to prevent recurrent symptoms. For example, a recommended daily dosage for vitamin D2 or vitamin D3 is 400 IU.

Vitamin D2 can be administered intramuscularly as an injection in an oil base, in a dosage of 500,000 IU or 12.5 mg every 2–3 months.

DETAILED DESCRIPTION

Figure 1:
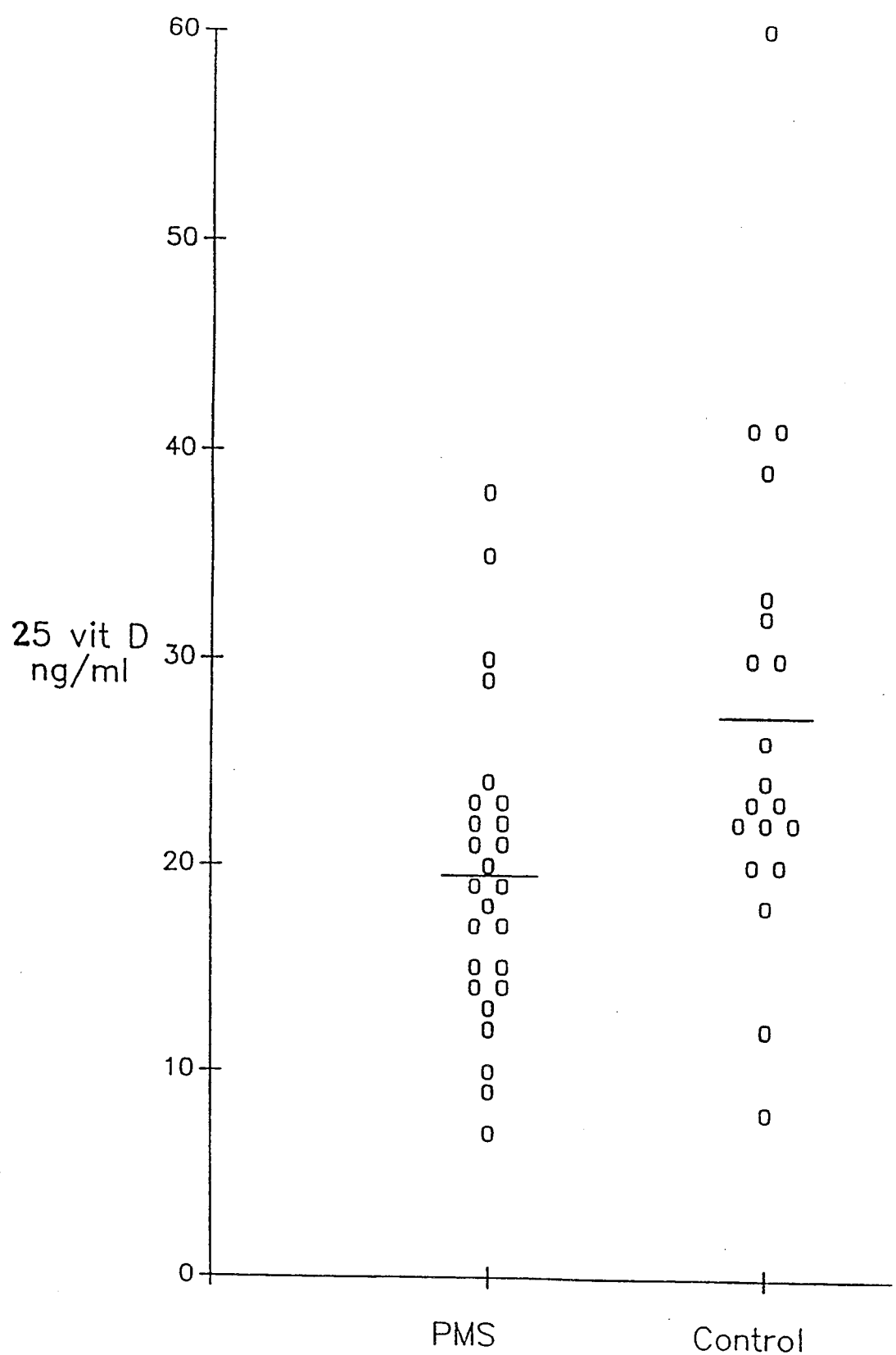
FIG. 1 compares the vitamin D levels in 26 women manifesting symptomatology of PMS with vitamin D levels in 20 asymptomatic controls.

A case control study was conducted exploring the role of vitamin D in PMS symptomatology. The study was designed to measure several parameters in women with PMS and compare these results with premenopausal asymptomatic controls. Through this research, it was possible to assess whether PMS is associated with low vitamin D levels.

The study was conducted in the Clinical Research Center and the outpatient department at Mount Sinai Medical Center. Subjects with PMS and controls were recruited by advertisement or privately referred. Those women who complained of PMS were screened for the PMS group; those who represented without symptoms of PMS were screened for the control group. Approximately one half of the candidates were eliminated during initial screening of preliminary information by telephone. The following were exclusion criteria for both groups: (1) history of amenorrhea, (2) menstrual cycle irregularity, (3) anorexia nervosa, (4) hyperparathyroidism, hyperthyroidism or hypothyroidism on dosages of levothyroxine greater than 0.05 mg per day, (5) major psychiatric disorder or active depression, (6) history of smoking more than one pack per day, (7) pregnancy, (8) perimenopause or menopause, history of endometriosis, mental retardation, (9) use of thiazide diuretics or anticonvulsants, (10) history of corticosteroid use, or (11) metabolic bone disease.

Participants for the PMS group were selected if: 1) they met preset criteria based on a prospective and consecutive 2 month daily diary: a pattern of clinically significant emotional and somatic symptoms that occur during the last week of the luteal phase and remit within a few days after the onset of the follicular phase, 2) they demonstrated a mean symptom intensity change of at least 50% in the luteal phase compared to the intermenstrual phase and 3) they had no history of metabolic bone disease or condition known to affect the bones. Controls were selected if they did not manifest symptoms of PMS based on the 2 month prospective diary.

The prospective assessment of daily symptoms for two menstrual cycles was obtained by means of a questionnaire which contained sixteen symptoms rated as absent, mild, moderate or severe and scored from 0 to 3. These sixteen symptoms were: nervousness, irritability, crying, mood swings, depression, increase or decrease in sleep, fatigue, difficulty in concentration, violent tendencies, abdominal bloating, headache, breast fullness, change in appetite, abdominal cramps, back pain, and craving for chocolate or salt.

Clinical evaluation involved a detailed medical, menstrual and gynecologic history, a physical examination and an extensive psychological screening which included the Beck Inventory Depression Scale, the Spielberg State Trait Anxiety Inventory, and the Premenstrual Assessment Form-past cycle version of Halbreich, Endicott and Schacht. The purpose of the mental health screening was to eliminate those women with psychiatric disorders, severe anxiety and depression.

Serum follicular stimulating hormone, luteinizing hormone, progesterone, magnesium, calcium, albumin, alkaline phosphatase, a complete blood count, and a 24 hour urine calcium excretion were obtained in all women during the luteal phase and measured by the clinical laboratories at Mount Sinai Medical Center. Both serum and urine calciums were measured using a colorimetric method on Beckman CX3 instruments. Calciotropic hormone samplings of 1,25 dihydroxyvitamin D [1,25(OH)2D], 25 hydroxyvitamin D [25O HD], intact parathyroid hormone (iPTH) were performed by USCF Hormone Reference Laboratory. Serum progesterone was measured during the last seven days of the menstrual cycle to confirm ovulation.

All participants, under prior instruction and supervision by a trained clinical research center's dietician, kept a detailed record of food intake for 3 days. The type of food consumed and the serving size of each portion for every meal and snack were reported. Portion sizes were estimated by the use of common kitchen utility measuring containers. Mean calcium intakes were determined for each subject by averaging the 3 daily intakes.

Final selection of the participants with PMS and controls was achieved by consensus among the internist, the psychiatrist, and the clinical social worker upon thorough review of the PMS diary, medical history and the psychological evaluation of each woman. All selected participants were caucasians, who gave informed consent in accordance with the policy established by Mount Sinai Medical Center's Institutional Review Board.

Bone mineral content of the lumbar spine and the proximal femur of all the women was determined by dual photon absorptiometry using the model DP3 system (Lunar Corp, Madison Wis.). Transmission scanning used a Gadolinium-153 source with two separate energy windows (44 and 100 KeV). The separate energies permitted the determination of the bone mineral content independent of the amount of soft tissue present. Bone mineral content (BMC) was measured in grams per centimeter; bone mineral density (BMD) as grams per square centimeter. BMD was derived by dividing the BMC by the area of the scanned bone.

The primary region of interest in the lumbar spine was L2 through L4. Vertebral BMD measurements were also determined for L1-4 and L1-2. For vertebral scanning of the lumbar spine L1-4, the body weight and height were measured. Subjects adopted the supine position with legs elevated over a cube to minimize lumbar lordosis. The iliac crest was identified by palpation and the probe placed in the scanning position at L5. Rectilinear scans (40 scan lines, line thickness 4.5 mm apart with a 2.5 mm/second speed) were performed on each subject.

The right proximal femur was scanned beginning at the symphysis pubis in the supine position, after the lumbar positioning cube was removed. An angular brace was strapped to the right ankle, and the right leg rotated as far as possible for best visualization of the femur. Bone mineral measurements were determined for the femoral neck, Ward's triangle and the greater trochanter.

All subjects were positioned and data analyzed by a single trained technician. The coefficient of variation and the long term reproducibility of these procedures in our center is ±2%.

Blood samples for measurement of parathyroid hormone, 1,25 dihydroxyvitamin D, and 25 hydroxyvitamin D, were collected in serum separator tubes, allowed to clot at room temperature for 30 minutes and immediately centrifuged for separation of the serum. Plastic pipettes were used to transfer the serum to plastic sample vials that were immediately frozen at −70 degrees Centigrade.

PTH was measured with an essay previously reported by Nussbaum with minor modifications. This assay is a two site immunoradiometric assay employing two polyclonal antibodies for the measurement of biologically active PTH (1–84). Only the intact PTH fragments form the sandwich complex necessary for measurement of the radiolabelled antibody. The assay used two goat antibodies to human PTH. One is specific for the PTH midregion or the C terminal (39–84) and is immobilized by adsorption onto 8 mm diameter polystyrene beads, and the other is radiolabelled for the N terminal region of PTH 1–34. The serum samples were assayed in duplicate. The intraassay and interassay coefficients of variation were 5.3% and 8.5% respectively. The normal range is 10 to 60 pg/ml. The assay is linear over the range of 10 pg/ml to 1650 pg/ml.

The 1,25 dihydroxyvitamin D samples were extracted by an acetonitrile method as described by Reinhards to remove proteins and lipids. Samples were purified on C-18 and Silica Sep-pak cartridges in a consecutive manner. A recovery sample was pipetted to measure the extraction efficiency of each sample. The purified extracts were then assayed in duplicate in a radioreceptor assay. The assay utilizes calf thymus binding protein which contains receptors which are specific for 1,25 dihydroxyvitamin D, permitting quantitative measurements in the range of 1.5 to 40 picograms per tube. The intraassay and interassay variations are 6.6% and 12.4% respectively.

The 25 hydroxyvitamin D samples were extracted using methanol to remove proteins and lipids. Extracts were then chromatographed on a Sep-pak cartridge in order to separate the 25 hydroxyvitamin D fraction from other vitamin derivatives. Recovery of 25 hydroxyvitamin D in each sample was monitored through the extraction and chromatography steps. The chromatographed extracts were assayed in duplicate in a competitive protein binding assay. Two dilutions were used to assure parallelism with standards. The assay utilized a naturally occurring vitamin D binding protein found in rat serum. The assay permitted quantitative measurements in the range of 1.5 to 40 picograms per tube. The intraassay and interassay variations for this assay were 10% and 15% respectively.

A total daily symptom rating score was derived by summing the 16 individual symptom ratings. Mean symptom scores for the different phases of the menstrual cycle were derived from the daily symptom ratings as follows:

| | |
|---|---|
| Luteal mean: | the average score of total symptoms for all cycles seven days prior to the onset of the menstrual period |
| Menstrual mean: | the average score of total symptoms for all cycles on the days of menstruation |
| Maximum Luteal: | the highest luteal average score for a single cycle |
| Maximum Menstrual: | the highest menstrual average score for a single cycle |
| Intermenstrual mean: | The mean of the total symptom scores during the seven days following the menstrual period for all cycles |

Quantitative comparisons between the PMS and the control groups were analyzed using t-tests for unpaired samples and the nonparametric Wilcoxon rank sum test. Nonparametric statistics were used when comparing symptom rating scores and BMD measures between PMS and control groups because of nonnormal data and/or unequal variances. Comparisons of the two groups on categorical data were performed using the chi-square statistic and Fisher's exact test. Pearson product correlation coefficients with 95% confidence intervals were calculated to assess the relationship between both luteal and menstrual symptomatology and various factors such as age, weight, BMD and calciotropic hormones. Statistical significance was based on two tailed tests at P values <0.05. Exact P values for the Wilcoxon test statistics were calculated using StatXact software for exact nonparametric inference.

One hundred thirty-eight adult outpatient women were initially screened for the trial. Twenty six women were selected for the PMS group, twenty for the controls. Ninety-two women were excluded based either on the above-described exclusion/inclusion criteria or noncompliance with the initial intake evaluation. The majority of the women were working women in professions such as law, medicine, nursing, social work and teaching. Most held full-time positions in their fields. All were white, middle to upper middle class women residing in the New York metropolitan area or suburbs, who were financially self-sufficient. As a group, they were knowledgeable of the clinical presentation of PMS and were well-informed from the media, self-help books and their own physicians about the current and available treatments for PMS. The majority of the women with PMS had attempted at least one form of recommended therapy with unsuccessful alleviation of their symptoms.

There was no difference in demographic features between the PMS and control groups as seen in Table 1. No statistically significant differences were detected for age, height, weight, body mass index, exercise, or history of smoking. The mean age (±SD) of the PMS women was 34.6 (±5.7) years, the controls 34.3(±6.0) years with a range of 28 to 42 years. The body mass index for both groups was 22 kilograms/square meter.

Biochemical and calciotropic hormone values were normal in both groups with the exception of 25OHD which were below the normal range of 10 ng/ml in two women with PMS and one control (Table 1). However, even within normal biochemical parameters, there were differences between the controls and women with PMS. Compared with normal controls, women with PMS had significantly lower 25OHD levels (19.5±7.5 vs. 25.3±8.3 ng/ml; t=2.46, df=44,P=0.018; [FIG. 1]) and higher serum calcium levels (2.4±0.1 vs. 2.3±0.1 mmol/liter; t=2.03, df=43, P=0.049). Serum cholesterol levels were significantly lower in the PMS group than in the controls (183.8±27.2 vs. 215.5±19.0; t=2.19, df-20, P-0.04). There were no differences between the two groups in the mean values of iPTH, 1,25(OH)2D, % calcium excretion, magnesium or albumin.

Dietary comparisons between the two groups are shown in Table 2. Phosphorus intake was significantly lower in the PMS group than in the controls (841.5±257.5 vs. 1022.8±171.2 mg; t=2.36, df=33, P=0.024). Mean 24 hour dietary calcium intakes were 726.5 mg. for the PMS group and 736.0 mg for controls. This did not prove significantly different. There were no differences in mean dietary intake of fat, carbohydrate, protein, cholesterol or calories.

The mean symptom scores for the luteal, menstrual and intermenstrual phases of the menstrual cycle in both PMS and control groups are shown in Table 3. As expected, the PMS group had significantly higher luteal symptom rating scores (luteal mean and maximum luteal) than controls (P=0.0000). Menstrual phase symptom rating scores (menstrual mean and maximum menstrual) were similarly higher in the PMS group compared to controls (P=0.0000). Intermenstrual symptom rating scores also differed between the PMS and control groups (P=0.0000). All participants with PMS demonstrated a mean symptom intensity change in the range of 500% in the luteal phase relative to the intermenstrual phase, well above the minimum change of 50% required by the inclusion criteria.

Figure 2:
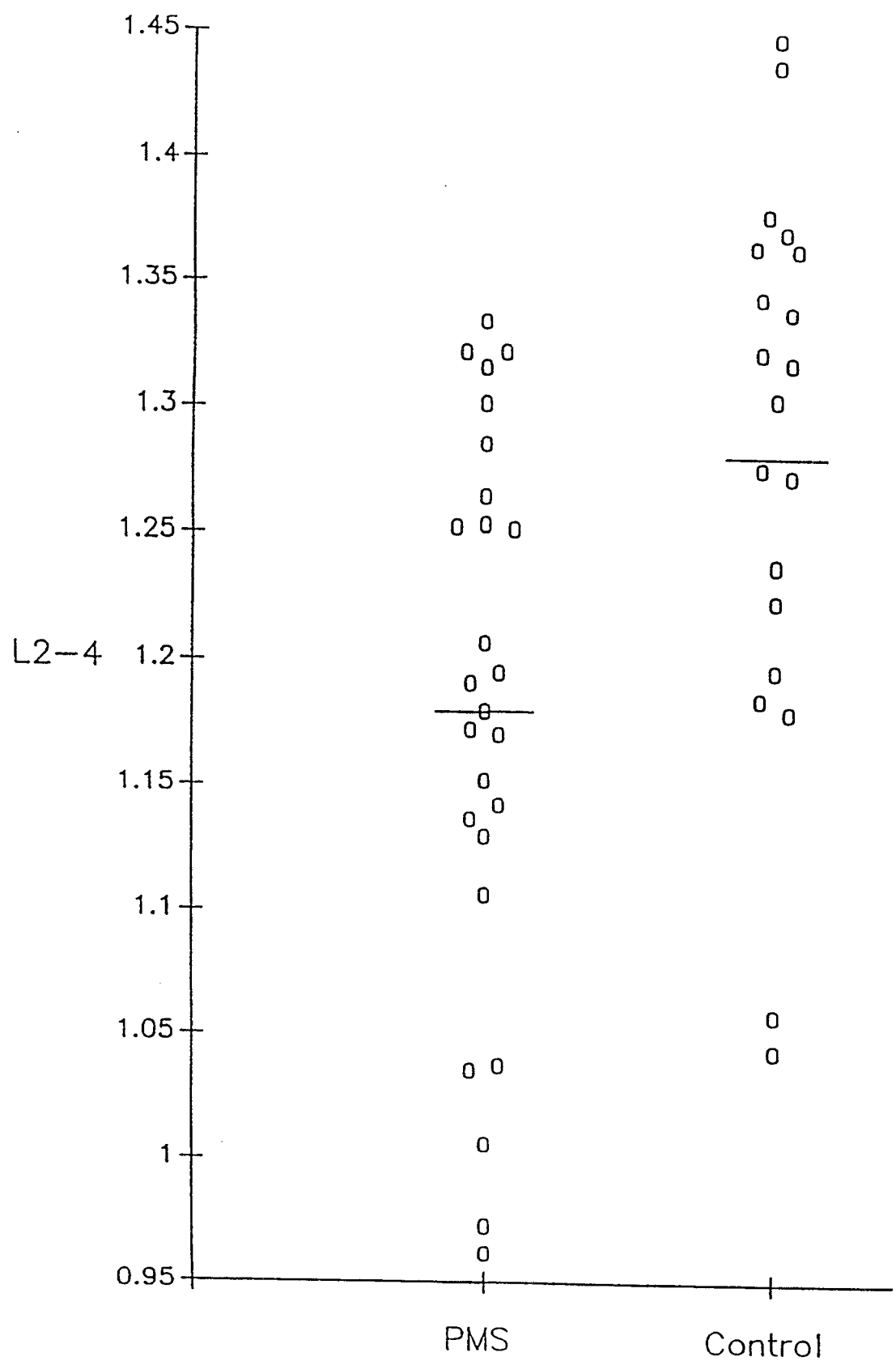
FIG. 2 compares the bone mineral densities at the lumbar spine L2-4 in 26 women with PMS with 20 asymptomatic controls.

Bone mass measurements were performed at the lumbar spine and the proximal femur for women with PMS and controls. Means and standard deviations on these measurements are shown in Table 4. The PMS group had reduced bone mass at the L2-4 site compared to controls. The mean ±SD BMD in the PMS group was 1.18±0.11 compared to 1.28±0.11 among controls (Wilcoxon rank sum Z=3.09, P=0.0016). A notable downward shift in the range of bone mass measurements at the L2-4 among the PMS participants is illustrated in FIG. 2. Bone mass was also reduced in the PMS group compared to the control group in the L1-4 site (1.17±0.10 vs 1.26±.11; Wilcoxon rank sum Z-2.89, P=0.0032) and in the L1-2 site (1.14±0.10 vs 1.24±0.11); Wilcoxon rank sum Z=2.95, P-0.0027). Of the femoral bone mass measurements, the Ward's triangle area was significantly reduced in the PMS group compared to the control group (p.84±0.10 vs. 0.91±0.16; Wilcoxon rank sum Z=2.00, P=0.0458). The groups did not differ in the BMD for the femoral neck or the trochanter.

Correlations between mean symptom scores and BMD and calciotropic hormone measurements were performed in both the total sample (Table 5) and the PMS group. Parathyroid hormone was negatively correlated with luteal symptomatology in the total group (r−0.30; 95% CI−0.54, −0.01). Dietary calcium negatively correlated with the menstrual mean (r=0.33,95% CI−0.60,0.01) and the maximum menstrual (r=−0.35;95% CI−0.61, −0.01). The spinal L2-4 BMD correlated −0.38 (95% CI−0.61 to −0.11) with luteal symptom scores, again consistent with the finding of significant differences between groups on the spinal BMD measurements. However, the correlation of L2-4 with menstrual symptom scores was smaller and had a 95% CI which included zero (r= −0.25; 95% CI−0.51 to 0.04). Similar patterns can be seen for the L1-4 and L1-2 measurements. To test whether higher luteal symptomatology was associated with lower bone mass, particularly in the spine, correlations between the spinal bone mass measurements and luteal symptom scores in the PMS group were computed. There was a reduction in the correlations when the analysis was limited to the PMS group. The correlation between L2-4 and luteal symptom scores was −0.18 (95% CI−0.52,0.22). The negative correlations between the spinal BMD measurements and luteal symptom severity can thus be attributed mainly to the differences between PMS and control groups in bone mass and not to a linear increase in symptom severity with reduced bone mass.

Consistent with total sample correlations, dietary calcium in the PMS group negatively correlated with menstrual symptom means. Serum calcium was negatively correlated with both luteal and menstrual symptom means. The correlations of luteal symptoms with iPTH seen in the total sample were not detected in the PMS group.

Many women may rate their symptoms differently according to their individual tolerance to pain. To control for this possibility, we used the intermenstrual symptom means as a covariate. The luteal and menstrual symptom means were correlated with the BMD and calciotrophic hormone measurements controlling for the intermenstrual symptom mean. The results which stand out in these analyses are the positive correlations between 1,25(OH)2D and luteal symptoms both in the PMS group (r−0.41; 95% CI 0.02,0.69; P-0.04) and the total sample (r=0.29; 95% CI 0.00,0.53; P-0.05).

The data demonstrated a significant difference in vitamin D between the two groups of women with lower levels of 250HD in the PMS group compared to controls. The reduced bioavailability of vitamin D may be reflective of inadequate formation of vitamin D from precursor 7-dehydrocholesterol or simply inadequate dietary intake. While two of our PMS participants had abnormally low 250HD levels, the majority had normal though lower levels compared to controls.

Both the PMS and control participants were white, premenopausal women who were similar in age, body composition and activity with no history of bone disease or menstrual disorders. The mean vertebral bone mineral density value at L2-4 (1.28 g/cm2±0.11) in our normal controls was comparable to that reported by Mazess et al for U.S. white women (1.26 g/cm2±0.13). Although the mean age of our participants with PMS was 34 years, the mean vertebral BMD of these participants at L2-4 (1.18 g/cm2±0.11) was equivalent to that of a woman 16 years older based on Mazess' age regression equation predicting spinal density. The standard deviations of 0.11 for the control group's vertebral BMD was comparable to the reported standard deviation of 0.13 for ages of 30 to 39. For the femur, our control's standard deviation was 0.10 to 0.16 compared to Mazess' report of 0.12 to 0.14.

Recent evidence in the pattern of bone loss has revealed a significant premenopausal bone loss in the appendicular and axial skeleton. The data shows a significant premenopausal vertebral and femoral bone loss in women with PMS. Other clinical surveys have similarly demonstrated a premenopausal bone loss in these two areas. In 1987, Mazess and colleagues showed premenopausal bone losses in their cross sectional data for the spine and femur with as much as 50% of the 20-25% reduction in spine and femur BMD evident prior to menopause. The longitudinal study by Riggs and colleagues noted a continuous and significant vertebral bone loss in 139 women of 1,32% per year before menopause and 0.97% per year after menopause. Significant bone loss from the axial skeleton was identified before menopause, while cortical bone loss as measured in the midradius remained insignificant.

High dietary calcium intake has been associated with increased serum calcium levels and suppression of parathyroid hormone. In the present study, women with PMS had higher serum calcium concentrations and lower 25OHD levels than controls. This was an unexpected finding. Lower serum concentrations of calcium had been expected, since correlations of mean symptom scores with serum calcium, dietary calcium and iPTH were negative ones, while those of 1,25(OH)2D were positive. A partial deficiency of vitamin D with low 25OHD levels can result in a secondary hyperparathyroidism with increased levels of 1,25(OH)2D. This may explain the positive correlations detected in 1,25(OH)2D levels with mean symptom scores. The secondary hyperparathyroidism that is expected in women with PMS may eventually be blunted from higher serum calcium levels with a resetting of the calcium set point.

The results of the present study indicate that women with PMS have reduced bone mass measurements compared to asymptomatic controls. The precise mechanism of the reduced bone mineral density in women with PMS is not known, although a long term partial vitamin D deficiency may be involved.

TABLE 1

CLINICAL AND BIOCHEMICAL CHARACTERISTICS OF THE WOMEN IN THE PMS AND CONTROL GROUPS

|  | PMS GROUP | CONTROL |
|---|---|---|
| Number of Subjects | 26 | 20 |
| Mean Age in years | 34.6 ± 5.7 | 34.3 ± 1.0 |
| Mean Age at Menarche | 12.4 ± 1.5 | 12.3 ± 1.0 |
| Number of Term Pregnancies | 0.46 ± 71 | 0.45 ± 89 |
| History of Smoking | 59.7% | 40.0% |
| Exercising regularly | 61.5% | 70.0% |
| Weight (kilograms) | 58.5 ± 7.7 | 59.9 ± |
| Height (centimeters) | 162.6 ± 5.0 | 162.6 ± 5.0 |
| Body Mass Index (kg/m2) | 22.3 ± 3.0 | 22.8 ± 1.8 |
| Alkaline Phosphatase (units/liter) | 61.5 ± 27.6 | 56.3 ± 16.2 |
| Serum Calcium (mmol/liter) | 2.4 ± 0.1* | 2.3 ± 0.1 |
| Serum iPTH (pg/ml) | 21.1 ± 11.0 | 25.1 ± 12.41 |
| Serum 1,25(OH)2D (pg/ml) | 37.8 ± 8.1 | 37.2 ± 6.1 |
| Serum 25OHD (ng/ml) | 19.5 ± 7.5** | 25.3 ± 8.3 |
| % Calcium Excretion | 1.4 ± 0.5 | 1.2 ± 0.7 |
| Serum Albumin | 4.5 ± 0.3 | 4.4 ± 0.7 |
| Serum Magnesium | 2.06 ± 0.23 | 1.96 ± 0.13 |
| Serum Creatinine | 0.87 ± 0.2 | 0.88 ± 0.2 |
| Serum Cholesterol | 183.8 ± 27.2* | 215.5 ± 19.0 |

Data are expressed as means ± standard deviations or percentages for yes/no answers.
*P value <0.05.
**P value <0.02.

TABLE 2

DIETARY CHARACTERISTICS OF THE WOMEN IN THE PMS AND CONTROL GROUPS

|  | PMS GROUP | CONTROL |
|---|---|---|
| Number of Subjects | 26 | 20 |
| Calcium (mg) | 726.5 ± 329.7 | 736.0 ± 164.1 |
| Carbohydrate (gm) | 184.7 ± 56.7 | 169.7 ± 40.3 |
| Protein (gm) | 64.2 ± 16.1 | 62.8 ± 12.1 |
| Fat (gm) | 57.8 ± 14.5 | 47.2 ± 18.9 |
| Caffeine (mg) | 270.7 ± 212.8 | 196.8 ± 152.1 |
| Cholesterol (mg) | 204.9 ± 67.1 | 185.6 ± 107.2 |
| Calories | 1535.6 ± 355.6 | 1401.3 ± 254.4 |
| Potassium (mg) | 2006.3 ± 522.1 | 2164.2 ± 552.5 |
| Sodium (mg) | 1679.2 ± 491.6 | 1887.4 ± 505.5 |
| Phosphorus (mg) | 84.1.5 ± 257.5* | 1022.8 ± 171.2 |
| Magnesium (mg) | 180.7 ± 72.7 | 207.3 ± 48.5 |
| Zinc (mg) | 5.7 ± 2.1 | 7.9 ± 4.3 |

*P value <0.05

TABLE 3

MEAN SYMPTOM SCORES FOR THE LUTEAL AND MENSTRUAL PHASES IN THE PMS AND CONTROL GROUPS

| MEAN SUMPTOM SCORES | PMS | Control | Rank Sum Z Statistic | Exact P Value |
|---|---|---|---|---|
| Luteal Phase |  |  |  |  |
| Luteal Mean | 13.3 ± 7.3 | 1.5 ± 1.4 | 5.618 | 0.0000 |
| Maximum Luteal | 16.3 ± 9.6 | 2.0 ± 1.6 | 5.652 | 0.0000 |
| Menstrual Phase |  |  |  |  |
| Menstrual Mean | 9.5 ± 6.4 | 1.9 ± 1.7 | 5.163 | 0.0000 |
| Maximum Menstrual | 12.1 ± 7.7 | 2.5 ± 2.0 | 5.231 | 0.0000 |
| Intermenstrual Mean | 2.6 ± 2.5 | 0.5 ± 0.8 | 3.915 | 0.0000 |

Data are expressed as means ± standard deviations.

TABLE 4

BONE MINERAL DENSITY MEANS

|  | PMS | Control | Rank Sum Z Statistic | Exact P Value |
|---|---|---|---|---|
| Spine |  |  |  |  |
| L2-4 | 1.18 ± 1.1 | 1.28 ± .11 | 3,092 | 0.0016 |
| L1-4 | 1.14 ± 1.0 | 1.24 ± .11 | 2.892 | 0.0032 |
| L1-2 | 1.17 ± 1.0 | 1.26 ± .11 | 2.947 | 0.0027 |
| Femur |  |  |  |  |
| Femoral neck | 0.94± .10 | 0.97± .14 | 0.798 | 0.4316 |
| Wards triangle | 0.84± .10 | 0.95± 18 | 1.996 | 0.0458 |
| Trochanter | 0.76± 11 | 0.80 ± .10 | 1.486 | .1398 |

Data are expressed as means ± standard deviations

TABLE 5

CORRELATION COEFFICIENTS BETWEEN MEAN SYMPTOM SCORES AND SELECTED BMD AND CALCIOTROPHIC HORMONE LEVELS IN THE TOTAL STUDY SAMPLE

|  | Luteal Mean | Max Luteal** | Menstrual Mean | Max Menstrual*** |
|---|---|---|---|---|
| Serum Calcium | −0.01(−0.30, 029) | 0.01(−0.29, 0.30) | −0.13(−0.41, 0.17) | −0.12(−40, 0.18) |
| iPTH | −0.30(−.54, −0.01)* | −0.30(−0.54, −0.01)* | −0.23(−0.49, 0.06) | −0.23(−0.49, 0.06) |
| 1.25(OH)2D | 0.14(−0.16, 0.41) | 0.19(−0.11, 0.46) | 0.03(−0.26, 0.32) | 0.04(−0.25, 0.33) |
| 25OHD | −0.19(−0.46, 0.10) | −0.17(−0.44, 0.13) | −0.19(−.46, 0.11) | −0.20(−.47, 0.09) |
| Dietary Calcium | −0.20(−0.50, 0.14) | −0.28(−0.56, 0.06) | −0.33(−0.60, 0.01) | −0.35(−0.61, −0.01)* |

| CORRELATION COEFFICIENTS BETWEEN MEAN SYMPTOM SCORES AND SELECTED BMD AND CALCIOTROPHIC HORMONE LEVELS IN THE TOTAL STUDY SAMPLE | | | |
|---|---|---|---|
| | Luteal Mean | Max Luteal** | Menstrual Mean | Max Menstrual*** |
| Spinal L2-4 | −0.38(−0.61, −0.11)* | −0.36(−0.59, −0.07)* | −0.25(−0.51, 0.04)* | −0.29(−0.53, 0.00)*** |

95% confidence limits for the correlation coefficients are given within parentheses.
* P value <0.05.
**Max Luteal is the abbreviated form of Maximum Luteal.
***Max Menstrual is the abbreviated form of Maximum Menstrual.

What is claimed is:

1. A method for treating premenstrual syndrome comprising administering to an individual in need of said treatment an effective dose of vitamin D so that the symptoms of premenstrual syndrome are significantly reduced.

2. A method according to claim 1 in which the dose of vitamin D is administered in the form of a vitamin D selected from the group consisting of vitamin D2 (ergocholecaliferol), vitamin D3 (cholecalciferol), and calcifediol.

3. A method according to claim 2 in which the oral dose of vitamin D2 and D3 is between 200 to 1,000 IU per day.

4. A method according to claim 2 in which the oral dose of vitamin D2 is between 50,000 to 200,000 IU weekly for 2-3 months.

5. A method according to claim 2 in which the oral dose of calcifediol is between 800 to 8,000 IU (20 to 200 ug) daily.

6. A method according to claim 4 in which the effective dose is administered for a time period of between 2 to 3 months.

7. The method according to claim 1 in which the vitamin D is administered intramuscularly as vitamin D2 500,00 IU or 12.5 mg in an oil base every 2-3 months.

* * * * *

UNITED STATES PATENT AND TRADEMARK OFFICE
CERTIFICATE OF CORRECTION

PATENT NO. : 5,354,743
DATED : October 11, 1994
INVENTOR(S) : Susan Thys-Jacobs

It is certified that error appears in the above-indentified patent and that said Letters Patent is hereby corrected as shown below:

Column 2, line 55
please change "ergocholecalciferol" to --ergocalciferol--;

Column 4, line 45
please delete "per centimeter";

Column 6, line 67
please change "df-20" to --df = 20--;
please change "P-0.04" to --P = 0.04--;

Column 7, line 39
please change "Z-" to --Z = --;

Column 7, line 41
please change "P-0.0027" to --P = 0.0027--;

Column 7, line 44
please change "(p.84 ±0.10" to --(0.84 ±0.10--

Column 7, line 53
please change "(r-0.30" to --(r = -0.30--;

Column 7, line 54
please change "(r = 0.33, 95%" to --(r = -0.33; 95%--;

Column 8, line 26
please change "(r-0.41" to --(r = 0.41--;
please change "P-0.04" to --P = 0.04--;

Column 8, line 27
please change "P-0.05" to --P = 0.05--;

UNITED STATES PATENT AND TRADEMARK OFFICE
CERTIFICATE OF CORRECTION

PATENT NO. : 5,354,743

DATED : October 11, 1994

INVENTOR(S) : Susan Thys-Jacobs

It is certified that error appears in the above-indentified patent and that said Letters Patent is hereby corrected as shown below:

Column 8, line 66
        please change "1,32%" to --1.32%--;

Column 9, Table 1, line 37
        please change "59.9 ±" to --59.9 ± 5.9--;

Column 10, Table 2, line 6
        under heading "PMS GROUP" please change "26 20" to --26-- and under heading "control", insert --20--;

Column 10, line 13
        under heading "PMS Group" please change "84.1.5" to --841.5--;

Column 10, Table 4, line 41
        under heading "Rank Sum Z Statistic" please change "3,092" to --3.092--;

Column 10, Table 4, line 48 (under heading "Control")
        please change "0.95 ± 18" to --0.91 ± .16--;

UNITED STATES PATENT AND TRADEMARK OFFICE
CERTIFICATE OF CORRECTION

PATENT NO.    : 5,354,743
DATED         : October 11, 1994
INVENTOR(S)   : Susan Thys-Jacobs Page 3 of 3

It is certified that error appears in the above-indentified patent and that said Letters Patent is hereby corrected as shown below:

Column 10, Table 4, line 50
   under heading "Exact P Value" please change ".1398" to --0.1398--;

Column 10, Table 5
   under heading "MAX Menstrual for Serum Calcium" please change "-0.12 (-40,0.18" to --0.12(-0.40,0.18--; and Column 11, lines 19-20
   please change "ergocholecalciferol" to --ergocalciferol--.

Signed and Sealed this

Twenty-third Day of January, 1996

Attest:

BRUCE LEHMAN

*Attesting Officer*      Commissioner of Patents and Trademarks